APPLE TREE
Filed March 17, 1966 2 Sheets-Sheet 1
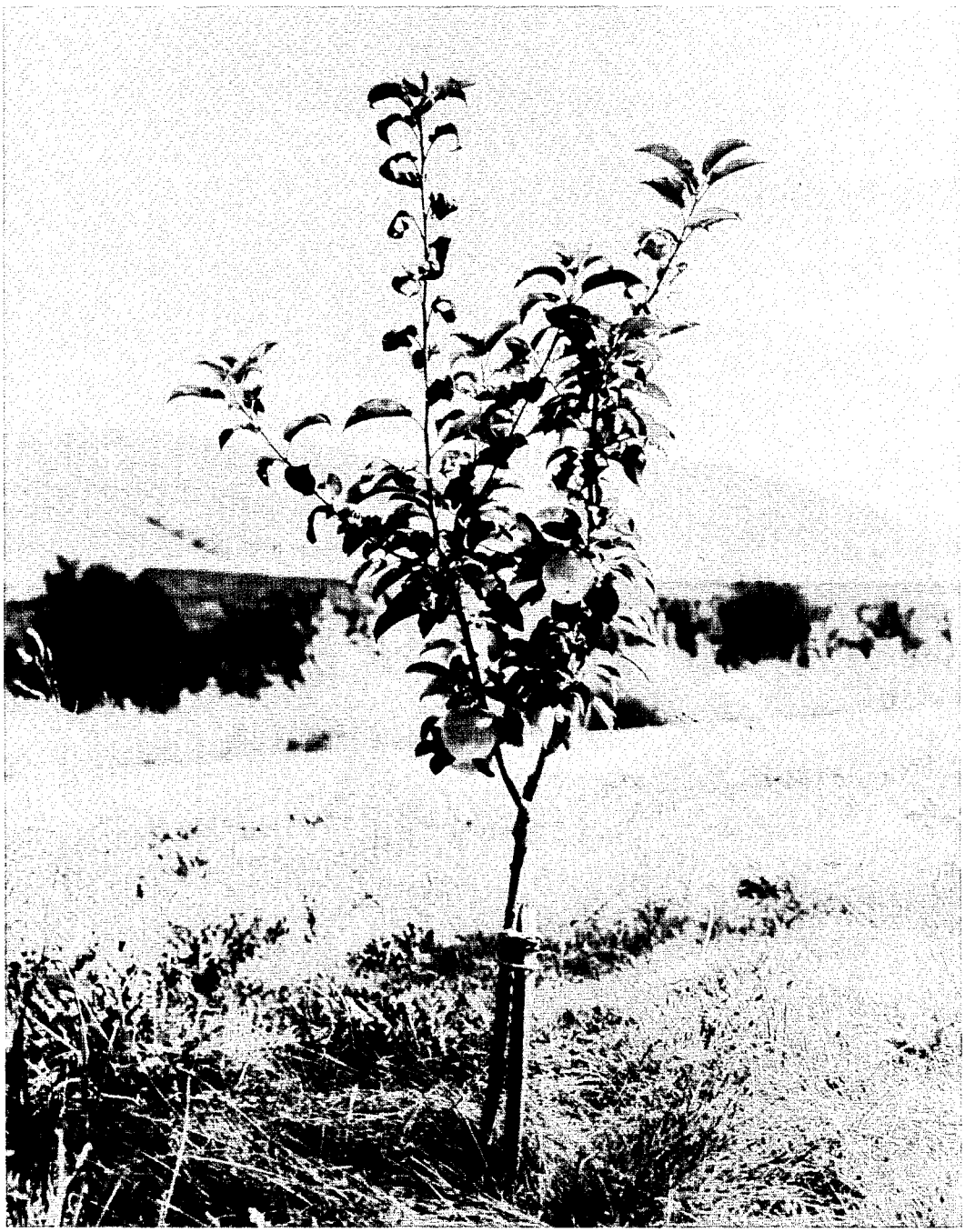
INVENTOR.
CALVIN L. COOPER
BY
Christensen, Sanborn & Mathews
ATTORNEYS APPLE TREE
Filed March 17, 1966 2 Sheets-Sheet 2
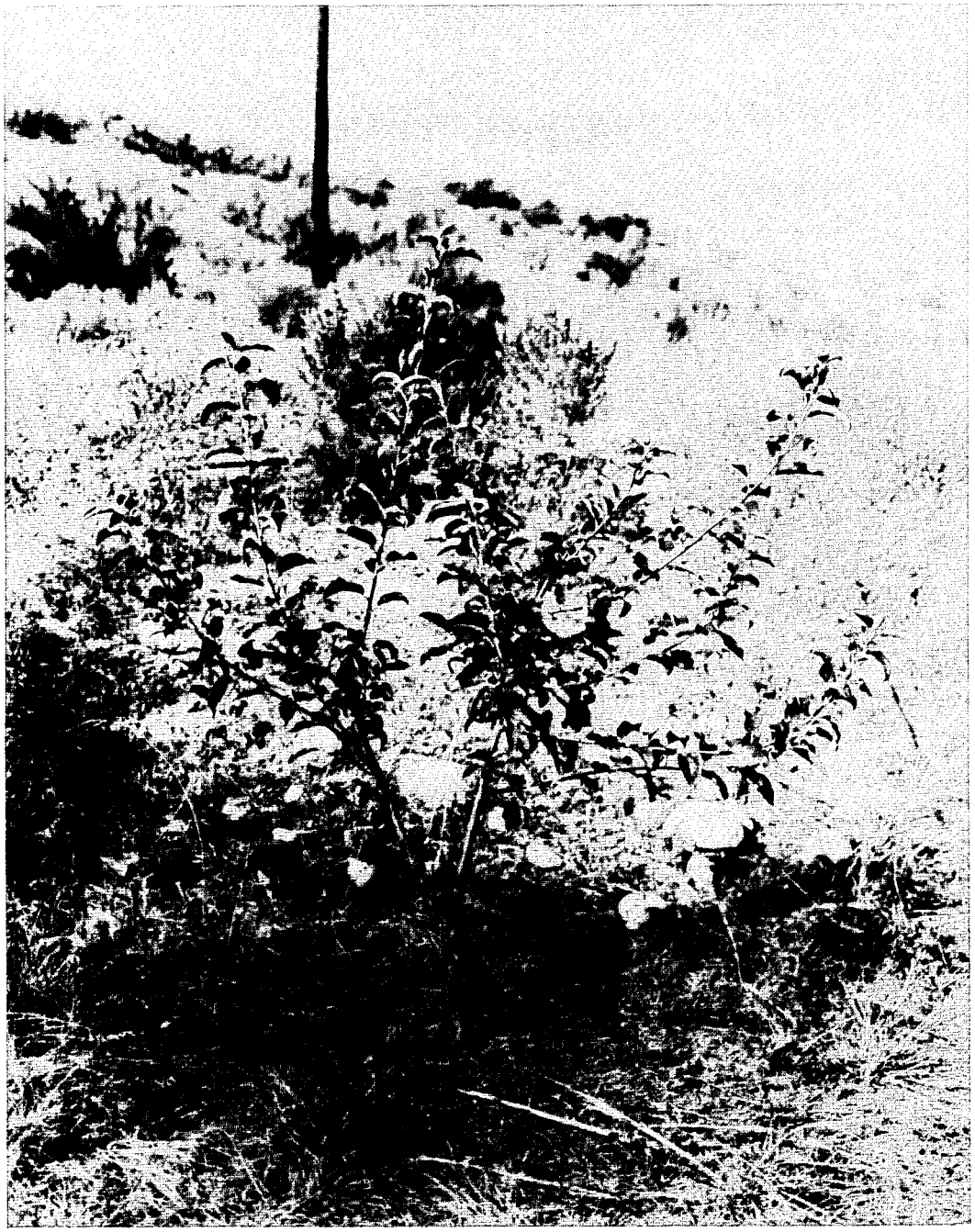
INVENTOR.
CALVIN L. COOPER
BY
Christensen, Sandborn & Matthews
ATTORNEYS United States Patent Office Plant Pat. 2,790
Patented Jan. 23, 1968

2,790
APPLE TREE
Calvin L. Cooper, Pateros, Wash. 98846
Filed Mar. 17, 1966, Ser. No. 535,254
1 Claim. (Cl. Plt.—34)

This invention or discovery relates to a new and distinct variety of apple tree originally discovered as a bud sport limb mutation growing on a Tydeman Early Red Worcester tree in the cultivated commercial orchard of applicant located near Brewster, Wash. The new variety has been asexually reproduced and its characteristics as hereinafter set forth have been proven stable.

In general the fruit of this new mutation seems to be identical to that of the parent tree, but the type or habit of growth of the spurs and limbs are distinctly different in that the branches show none of the undeveloped buds that are common on the parent variety. Moreover, there is less distance between spurs on the new variety and a tendency to set fruit better than in the case of the parent. The lesser distance between nodes in the new variety gives its limbs a spur type appearance. The closer spacing of the spurs on the new variety compare with that of the other limbs of the parent Tydeman tree in a manner similar to the comparison between spur types of Delicious as against conventional types of Delicious.

A distinctively unique advantage of the new variety is its reduction in vigor, its early fruit bud formation and early bearing characteristic typical of compact sports in other varieties (i.e. Delicious and Golden Delicious) but heretofore undiscovered in Tydeman's Early Worcester. The original Tydeman Early Worcester apple is inclined to be willowy, over-vigorous in growth and slow to commence bearing. By ameliorating these characteristics of the original Tydeman, the new mutation should prove to be a valuable addition to commercial culture of the Tydeman apple.

The accompanying drawing comprises a photograph of a young tree of the new variety and, for comparison, a photograph of a young tree of the original Tydeman variety of the same age and growing on the same type of root stock within several feet of the former.

Tree: medium size; vigorous; dense; hardy; productive; regular bearer.

*Trunk.*—Stocky; smooth.

*Branches.*—Thick; smooth. Color—deep grayish-olive, Plate XLVO, Color No. 21'''', tone *i* (Ridgway). Lenticels—medium number, medium size. Leaves—medium large, medium thickness, rugose; length—about 4 inches; width—about 2¼"; shape—ovate-taper pointed; color—dark dull yellow green, Plate XXXII, Color No. 31", tone *m* (Ridgway); margin—serrations moderately dull, fairly regular, shallow; petiole—medium long (1"–1¼"), medium thickness.

Flower: Medium time, medium larger. Color—white with faint carmine tinge.

Fruit:

*Maturity.*—Same as parent.

*Size.*—Uniform. Axial diameter—3". Transverse diameter—3½" diameter.

*Form.*—Roundish oblate.

*Cavity.*—Symmetrical, acute, slightly russet. Depth—¾". Width—1⅛".

*Basin.*—Symmetrical, angular. Depth—7/16". Width—1".

*Stem.*—Medium slender, pubescent. Length—1".

*Calyx.*—Closed; segments persistent; acute; convenient; length, 5/16". Outer surface—pubescent. Inner surface—pubescent.

*Skin.*—Medium thin, tough, smooth, oily. Dots—inconspicuous, small, few. Ground color—marius yellow, Plate IV, Color No. 23, tone *f* (Ridgway). Color markings—from carmine, Plate 1, Color No. 1, tone *i* (Ridgway), to ox-blood red, Plate I, Color No. 1, tone *h* (Ridgway). Bloom—slight bloom. General color effect—red.

*Flesh.*—Rather juicy. Color—white with yellowish tint. Texture—medium firm, medium fine. Flavor—subacid, mild. Aroma—distinct. Quality—good.

*Core.*—Medium. Bundle area—medium; cordate; symmetrical at base; acute at base. Halves of core—equal. Bundles—inconspicuous, green tinged. Core lines—clasping. Carpellary area—distinct, medium large. Calyx tube—pubescent, cone shaped; entire depth—⅜". Styles— present, united toward base. Stamens—in one median whorl. Seed cells—open, axite; cell walls—thick, tough; length—7/16"; breadth—⅛". Longitudince section—broadly ovate, acute at apex; surface fissured; cross-section—broad.

*Seeds.*—Number—6–10 perfect, usually 2 or 3 imperfect; 2 per cell. Length—5/16". Breadth—3/16". Form-acute. Color—mars brown, Plate XV, Color 13', tone *m* (Ridgway).

Having thus disclosed my improved variety, I claim:

1. The new and distinct variety of apple tree shown and described.

No references cited.

ROBERT E. BAGWILL, *Primary Examiner.*